United States Patent
Maltin (10) Patent No.: US 6,733,671 B1
(45) Date of Patent: May 11, 2004

(54) APPARATUS FOR TREATING FLUIDS

(76) Inventor: Christopher Maltin, Goulds House Horsington, Somerset, BA8 0EW (GB)

( * ) Notice: Subject to any disclaimer, the term of this patent is extended or adjusted under 35 U.S.C. 154(b) by 0 days.

(21) Appl. No.: 10/110,092

(22) PCT Filed: Oct. 12, 2000

(86) PCT No.: PCT/GB00/03922
§ 371 (c)(1),
(2), (4) Date: Apr. 8, 2002

(87) PCT Pub. No.: WO01/27041
PCT Pub. Date: Apr. 19, 2001

(30) Foreign Application Priority Data

Oct. 12, 1999 (GB) ............................................... 9924087

(51) Int. Cl.$^7$ ............................................... B01D 63/00
(52) U.S. Cl. ............................... 210/321.6; 210/198.1; 210/197; 210/220; 210/221.2; 210/346; 210/620; 210/170; 366/105
(58) Field of Search .......................... 210/321.6, 198.1, 210/197, 220, 221.2, 321.84, 321.75, 488, 489, 346, 620, 758, 651, 776, 170, 257.1, 258, 167, 180, 181, 188, 189; 366/105–107

(56) References Cited
U.S. PATENT DOCUMENTS 4,142,975 A    3/1979    Kinzer

FOREIGN PATENT DOCUMENTS

EP    0 713 709 A    5/1996
GB    2 305 369 A    4/1979

OTHER PUBLICATIONS

Patent Abstracts of Japan, vol. 013, No. 124 (c–580), Mar. 27, 1989 & JP 63 295402 A, Dec. 1, 1988.

Patent Abstracts of Japan, vol. 007, No. 285 (c–201), Dec. 20, 1983 & JP 58 163490 A, Sep. 28, 1983.

*Primary Examiner*—W. L. Walker
*Assistant Examiner*—K S Menon
(74) *Attorney, Agent, or Firm*—Gifford, Krass, Groh, Sprinkle, Anderson & Citkowski, P.C.

(57) ABSTRACT

Treatment apparatus comprising a chamber (11) for treatment of a process fluid and having at least two regions in each of which the process fluid is caused to follow a circulating path, in which the location of openings (13, 14) for introduction and removal of process fluid to and from the chamber and the shape of means defining the paths followed by the components of the process fluid through the chamber is such that the circulating paths followed by the process fluid in the two regions have oppositely directed radial components and the two regions communicate with one another such that process fluid introduced into one region is constrained to flow into the other region before leaving the vessel, at least part of the chamber wall (12') being formed as a semi-permeable membrane.

14 Claims, 5 Drawing Sheets

APPARATUS FOR TREATING FLUIDS

The present invention relates generally to the treatment of process fluids and particularly, although not exclusively, the treatment of slurries comprising solids in liquids.

One technical field in which such slurries occur is in the treatment of organic material by bacteriological action, especially the so-called slurry digestion processes which are known for the treatment of organic waste materials.

One of the problems encountered in the treatment of process fluids both with bacteriological and other processes lies in the possibility of non-uniform treatment due to differences in the conditions encountered by the process fluid as it passes through the treatment system, and especially on differences in the residence time of the material within the system.

Where bacteriological action is involved, which frequently takes a relatively extended time period for completion, any material which follows a shorter than average route through the process material may be inadequately treated. This is unacceptable in the circumstances where the treatment processes is a biological breakdown of waste products because the resulting, partially-treated material may not be suitable for the uses to which the fully-treated material may be put. For example, biological breakdown of organic waste material such as animal excrement produces, when the treatment is complete, a residual solid material which is odour free and high in nutrients suitable for use as a horticultural or agricultural fertiliser. Inadequately treated material, on the other hand, may not be odour free, and more importantly may contain biological contaminants, pathogens or seeds the former of which could be dangerous or at least detrimental and the latter of which, if still viable may reduce the value of the material as a fertiliser.

Process fluids may also have constituents, such as salts or heavy metals the presence of which is unwanted or even dangerous. The present invention seeks, therefore, to provide apparatus for the treatment of process fluids in which means are provided by which the content of such unwanted components can be at least reduced.

The applicant's own earlier British Patent Application GB-A-2 305 369 discusses apparatus for the treatment of process fluids of the general type having a vessel within which the process fluid is caused to circulate by the introduction of a stream of bubbles. By contrast Japanese publication JP-A-63295402 discloses a reactor at least part of the wall of which is formed with a hydrogen permselective membrane and an outer tube concentric with the reaction chamber.

According to the present invention there is provided treatment apparatus comprising a chamber for treatment of a process fluid and having at least two regions, means for causing the process fluid to follow a circulating path in each said region, the two regions communicating with one another such that process fluid introduced through an inlet into one region is constrained to flow into the other region before leaving the vessel, characterised in that at least part of the chamber wall in which an outlet is located is formed as a semi-permeable membrane contacted intimately by the process fluid following the said circulating path.

This allows for a selective transfer of material across the semi-permeable membrane, which may be made selective for those materials it is desired to remove. The circulating flow of the process fluid ensures that it comes into intimate contact with the semi-permeable membrane, especially in embodiments in which the outlet is located in an end wall such that the process fluid swirls around an outlet creating a vortex and causing the fluid to pass in close contact with the surface of the end wall. It is also possible for other walls to be formed entirely or partly as semi-permeable membranes, or even for all the walls defining the said chamber to be semi-permeable membranes. This is of particular relevance if the chamber is formed as a vessel immersed in a liquid bath or lagoon containing a liquid the composition of which encourages transfer of selected materials across the same semi-permeable membrane.

Embodiments of the invention may be made in which there are a plurality of chambers separated from one another by double-skinned partitions themselves defining compartments housing fluids co-operating in the transfer of selected materials across the semi-permeable membrane.

In one-embodiment of the invention a chamber for receiving a treatment fluid has a least two generally unobstructed interior regions in each of which the process fluid is caused to follow a circulating path, in which the means defining the overall paths of different parts of the process fluid between an inlet and an outlet to the chamber results in the path lengths being not substantially different for substantially all parts of the process fluid, and at least part of the chamber wall being formed as a semi-permeable membrane contacted by a process fluid in its circulating flow.

The inlet opening in the apparatus may open directly into one of the said two regions, and the outlet may correspondingly communicate with the other of the said two regions, the arrangement being such that process fluid introduced into the said one region through the inlet circulates in the said one region before transferring to the second region in which it circulates in contact with the semi-permeable membrane before leaving through the outlet.

Embodiments of the present invention may be formed as a treatment vessel for a process involving biological action on organic process materials comprising a solid/liquid, or liquid/liquid slurry or mixture, in which circulation, of the process material is driven by introducing gas at a low level within the vessel and allowing bubbles thereof to rise, with a collection region for solids from which solids can be extracted for further treatment.

In a preferred embodiment of the invention the bubble inlets are arranged in a plurality of rows thereof whereby to provide a "curtain" of bubbles. In a vessel configuration such as that outlined above, in which the vessel has two regions in which the process fluid is caused to circulate in opposite directions, and in which the transfer of the process fluid from one to the other takes place in its transit through the vessel, the circulation-driving bubbles may form a "curtain" between the two regions such that the process fluid must pass across the curtain of bubbles in its transit through the vessel. Any relatively dense particle of solid material entrained with the process fluid will, on passing through the bubble curtain, experience a significant reduction in its buoyancy thereby falling to the solids-collection region.

A configuration in which two rows of bubble inlets are provided may have a channel between the two rows of bubble inlets serving as this collection region, and such channel may house an auger or other means for driving the solid particles collecting therein towards a distribution point from which they can be removed from the vessel.

Removal of such solids from the vessel may involve the use of a water column within which the solids may be elevated, for example by means of a further auger or a gas lift apparatus, and which serves to maintain the gas tight closure of the vessel while nevertheless allowing solids to be extracted therefrom.

Regardless of the form of the vessels (and certain preferred configurations[]will be described hereinafter in more detail) a treatment system for a process fluid may comprise a plurality of such vessels in sequence, so arranged that different processes take place in different vessels.

As an example, one embodiment of the present invention may comprise a treatment system for a process fluid comprising or including organic materials to be broken down by bacteriological action, comprising a plurality of chambers interconnected to receive the process fluid in sequence, each chamber having means for controlling at least one process parameter, and means for introducing fluid into the chamber in addition to the process fluid. There may further be provided means for directing process fluid from the outlet of a chamber to an inlet of the same chamber or to an inlet of another chamber upstream or downstream in relation to the flow of process fluid through the system.

The parameters which may be controlled within the chambers comprise the temperature of the process fluid within the chamber, the pressure within the chamber, the rate of flow of process fluid through the chamber, the precise bacteriological content of the chamber (in the case of biological processes, which may be achieved by introducing particular bacteria into it for inoculating the material therein) and/or the introduction or presence of other process reagents, in particular liquids or gases.

The introduction of a gas into the treatment vessel may be undertaken simply to drive the circulation of the process fluid within the vessel, in which case the gas may be chosen as one contributing to the maintenance of aerobic or anaerobic conditions as the case may require, or alternatively the gas may be one which takes part in the reaction proceeding within the vessel.

Whether the plurality of chambers are formed as compartments within a vessel by partitioning, or whether they are formed as separate vessels interconnected by ducting, it is preferred that at least some of the walls defining the chamber are in contact with a heat exchange fluid which can be driven in counter current with respect to the direction of flow of process fluid through the system. In this way, for example, exothermic reactions taking place in some of the chambers can be cooled by the heat exchange fluid and the heat transferred to other chambers whereby to raise the temperature of the material therein.

Various embodiments of the present invention will now be more particularly described, by way of example, with reference to the accompanying drawings, in which.

Figure 1:
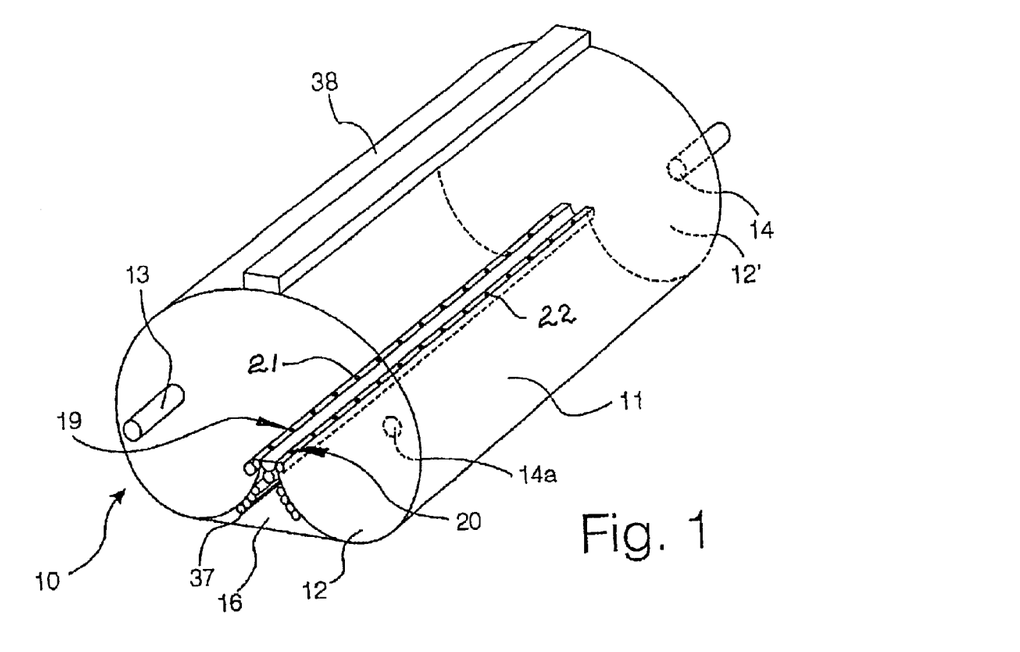
FIG. 1 is a perspective view of a vessel formed as a first embodiment of the invention.

Referring now to FIG. 1, the embodiment illustrated comprises a single elongate tank of cardioid type cross section as described in more detail in the applicant earlier GB Patent Application No. 9519499.9 and International Patent Application No. PCT/GB96/02336 (publication no. WO 97/11915. The vessel 11 has an end wall 12 with an inlet duct 13, and an opposite end wall 12' with an outlet duct 14.

The cross sectional shape of the vessel 11 (as illustrated more clearly in FIG. 2) gives rise to two separate regions generally indicated 17, 18 separated by a central median plane of symmetry X—X (FIG. 2) on either side of which are located elongated gas delivery pipes 19, 20 having rows of holes 21, 22 from which, in use, two rows of bubbles 24, 25 (FIG. 2) rise to form a "curtain" of bubbles. The inlet duct 13 at one end of the vessel 11 opens into a first region 17, on one side of the curtain of bubbles 24, 25 and the outlet duct 14 leads from the other region or chamber 18, so that process material introduced into the vessel 11 is caused to circulate first in one direction (anticlockwise as shown in FIG. 2 by broken line arrows A) as it passes along the first region and is caused to transit from one region 17 to the other region 18 across the curtain of bubbles 24, 25 where it circulates in the opposite direction (clockwise as viewed in FIG. 2) as it passes through this region before exiting from the vessel 11 through the outlet 14.

In its passage across the curtain of bubbles 24, 25 any heavy particles of dense material entrained with the process fluid experience significantly less buoyancy, due to the presence of the bubbles, than they experience within the regions 17, 18, resulting in these particles falling into a collection channel 26 located between the two rows of openings 21, 22 from which the introduced gas flows.

Figure 2:
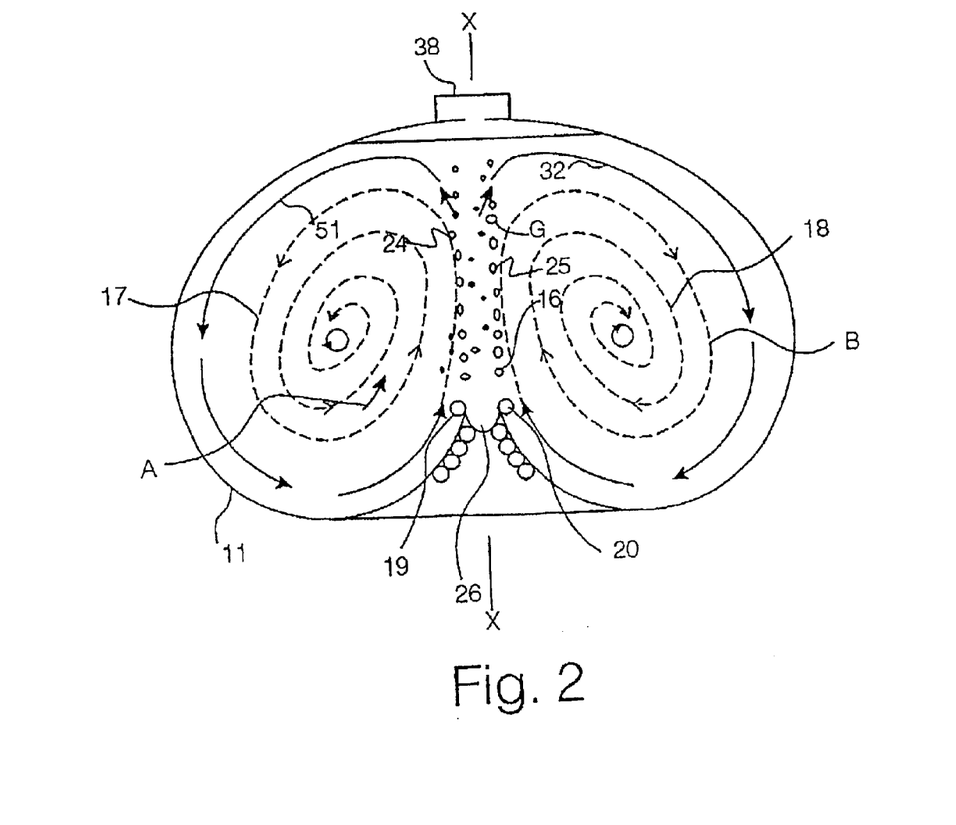
FIG. 2 is a sectional view through the embodiment of FIG. 1.

In its circulating flow within the region 17 the process fluid follows a spiral path gradually increasing in diameter as it travels along the length of the vessel 10, and conversely within the region 18 it follows a spiral path of gradually decreasing diameter as represented by the broken line arrows B in FIG. 2. The actual path followed by an individual particle, therefore in its spiral flow around the region 17, gradually increasing in diameter and travelling along the length of the chamber 10, (and the corresponding circulating path around and along the region 18) extends for a distance many times greater than the length of the vessel 10. This extended circulating path means that the residence time of each particle is always at least a minimum value represented by the transit time along one of the regions 17, 18. In fact the residence time for each particle is substantially the same as that of all the other particles because there is no alternative route by which a particle may inadvertently pass from the inlet duct 13 to the outlet duct 14 along a path less than that travelled by the other particles thereby receiving less treatment within the vessel. For example, if a particle remains within the region 17 while travelling along the entirety of its length before crossing to region 18 it will be located at the outlet end and pass relatively quickly to the outlet 14. Another particle may circulate to a radially outer position in the region 17 quickly and pass across the curtain into region 18 while still close to the inlet end. This particle now has to travel the full length of the vessel before reaching the outlet 14 following a spiral path which has substantially the same length as the path followed by the particle first described.

Figure 5:
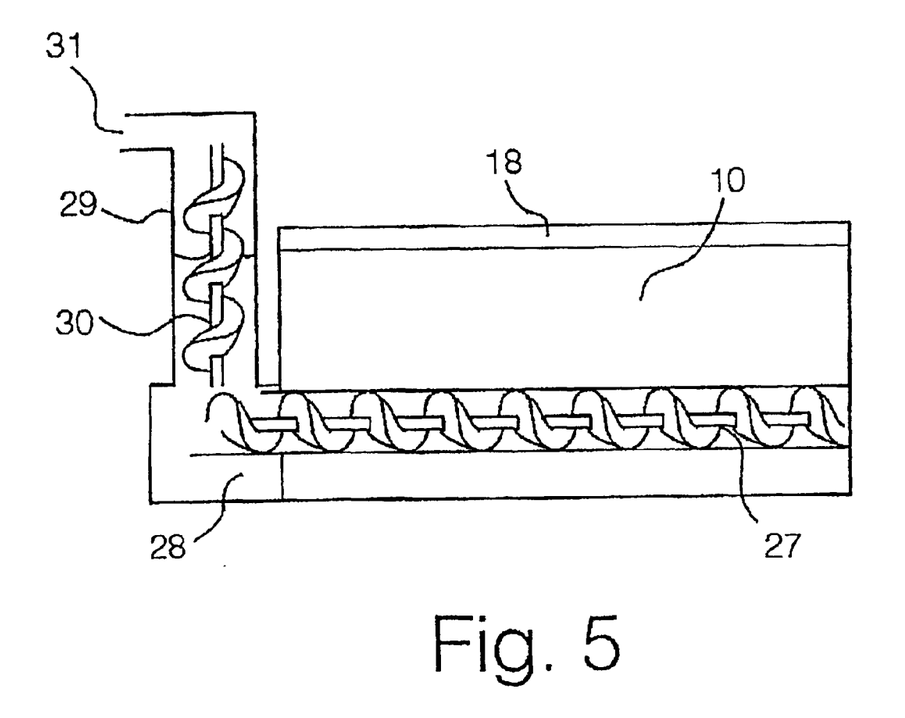
FIG. 5 is a side view of a vessel formed as a further embodiment of the present invention.

The collection channel 26 for heavy particles houses an auger 27, as illustrated schematically in FIG. 5, which exits into a closed chamber 28 from which extends an upright column 29, filled with the process liquid. This column 29 houses a vertical auger 30 leading to an outlet 31. Particles collecting in the channel 26 are thus conveyed first to chamber 28 and then out along the column 29 rising above the surface of the treatment fluid and leaving through the exit 31 from where they may be segregated; those particles which may be treated by the process (for example dense lumps of organic material) may be broken down and reintroduced into the process fluid, while those which cannot be processed with this treatment are recycled to other uses.

Figure 3:
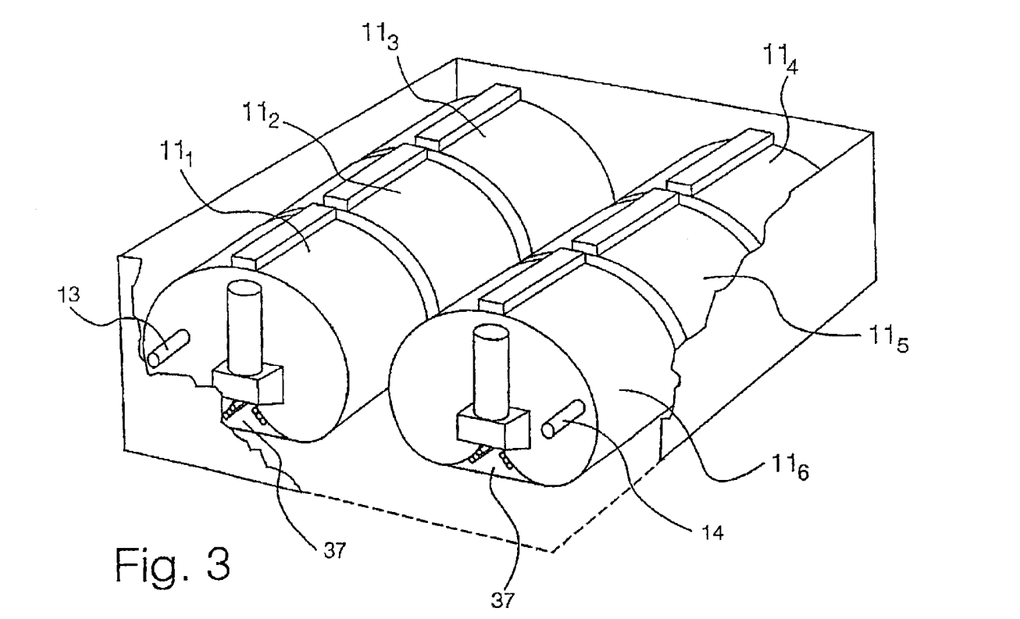
FIG. 3 is a schematic perspective view of an array of vessels forming a treatment system formed as an embodiment of the present invention.
Figure 4:
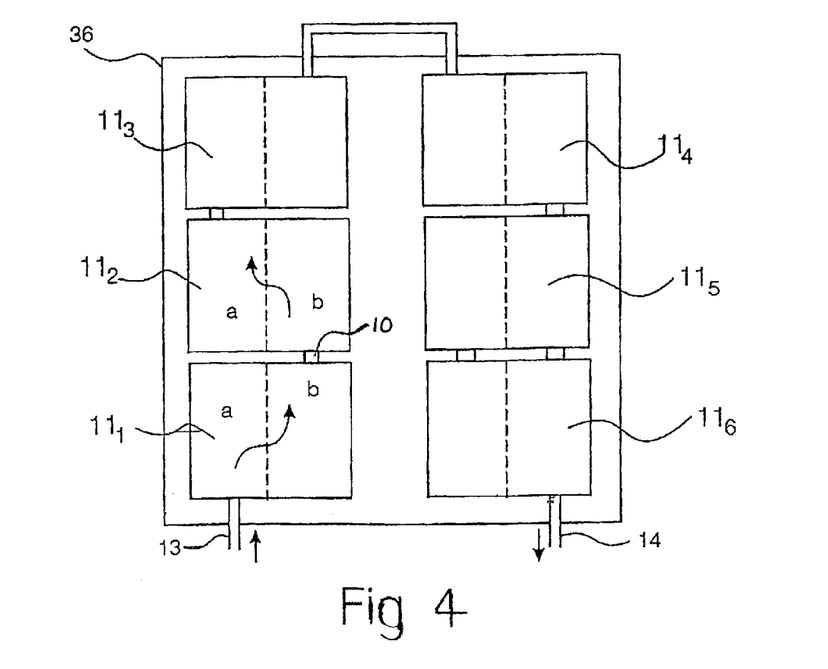
FIG. 4 is a plan view from above of the array of FIG. 3.

FIGS. 3 and 4 illustrated a system comprising a plurality of vessels (in this embodiment six are illustrated although the array may comprise 4, 8 or a larger number of vessels. Each vessel 11 in the array has been identified with an appropriate suffix$_1$ through $_6$ to identify its position in the sequence. As can be seen in FIG. 4 each vessel 11 is connected to the next vessel in the sequence on alternate sides a or b such that the inlet duct 13 to vessel $11_1$ opens into the left hand region a and the intercommunicating ducts 35 leading from region b of vessel $11_1$ opens into region b of vessel $11_2$.

The circulating flow within each side lobe of each vessel results, as described above, in a flow path comprising a spiral helix, which is represented by the curved arrow in each vessel illustrated in FIG. 4, it being appreciated that each flow path is represented only schematically and that no particle actually follows the path of the arrow but rather the more convoluted, extended path described in relation to FIGS. 1 and 2.

The vessels 11 are all contained within a bath or lagoon 36 (shown systematically) which is filled with a liquid to the same level as the process fluid in the tanks to equalise the pressures across the tank wall making it possible to use relatively thin sheet material, typically plastics, to contain the process fluid without requiring extremely high mechanical strength. The lagoon 36 may be formed as a pit for this reason.

Beneath the central cusp part of each vessel 11 is a heat exchanger 37 fed with heat exchange fluid as will be described in more detail below. The application of heat at this part of the vessel encourages convection currents which reinforce, and may even replace the forced circulation generated by the introduction of gas bubbles at the cusp.

In use of the apparatus described in relation to FIGS. 3 and 4, particularly in relation to a process fluid comprising a slurry of organic waste material, aerobic or anaerobic breakdown of the organic animal and/or plant materials takes place giving rise to simple substances. These may include a high proportion of gaseous and soluble products. The gaseous products, which in particular may include methane, are drawn off from the manifold 38 (see FIGS. 1 and 2) at the top of e vessel 11, or rather from the top of each of those vessels 11 in which the gaseous products are produced.

Of course, gaseous products are not necessarily immediately produced as the process taking place in the first vessel or chamber after introduction may comprise no more than preliminary aeration, with air being bubbled in as the circulation-driving medium. Only excess gas from this process is drawn from the first manifold. Thereafter, an anaerobic digestion process may take place which involves the cleaving, by extracellular enzymes, of polysaccharides, lipids and proteins, which are broken down to form sugars, fatty acids and glycerol. This initial part of the breakdown process, which for example takes place in vessel $11_2$, does not immediately give rise to gaseous products either. The preliminarily treated process fluid then passes into vessel $11_3$ and the process continues with the onset of fermentation by various organisms resulting in products which may include acetate, butyrate, ethanol, lactate, propionate and succinate together with carbon monoxide and hydrogen. These processes are very complex and this outline is intended only as an indication of some of the processes at work. The carbon monoxide and hydrogen are connected by bacteriological metabolisation to acetate by some of the bacteria present, whilst other bacteria may convert the carbon monoxide and hydrogen to methane.

The other vessels $11_4, 11_5$ etc may be colonised by different bacteria due to the different conditions existing or set up in these vessels, such as temperature, pressure, flow rate etc. These bacteria may for example metabolise ethanol, lactate and other products of the initial fermentation resulting in acetate and hydrogen.

The temperatures at which the various bacteriological and/or other processes take place can be controlled by suitable means (not shown) including control of the heat exchangers 37.

The rate at which gases are introduced into the gas delivery pipes 19, 20 determines, together with the convection currents set up by the heat exchangers 37, the speed of circulation of the process fluid within the vessels and can be controlled independently (by means not illustrated). The residence time of the process fluid within the various vessels may also be controlled by means (not shown) such as bypass valves, shunt valves, subsidiary holding vessels, shut off valves, feedback or recirculation loops and the like. The choice of gas to be introduced as the circulation-driving gas through the duct 19, 20 may be air, for example in the first and last of the vessels $11_1$ and $11_6$ whereas methane may be introduced into the intermediate vessels $11_2, 11_5$ and an inert gas into vessels $11_3, 11_4$. The methane may of course be that generated by the digestion process itself. This may be recycled directly or drawn from storage containers.

The resulting digested slurry output from the last vessels $11_6$ in the series can then be passed to a separator where the solids are separated from the liquids to yield an odourless fertiliser rich in nutrients and a liquid which may also be used as a fertiliser (depending on the process fluid in question and the precise treatment process) or may be discharged perhaps after further final purification treatment.

In an alternative embodiment (not illustrated) the extraction of unwanted solids from the vessels as described in relation of FIG. 5, may incorporate the use of a pump in place of the auger 30 in the column 29, pumping a "plug" of water along the ducts to the outlet 31, or a gas lift system, especially one using air, may be employed.

Figure 6:
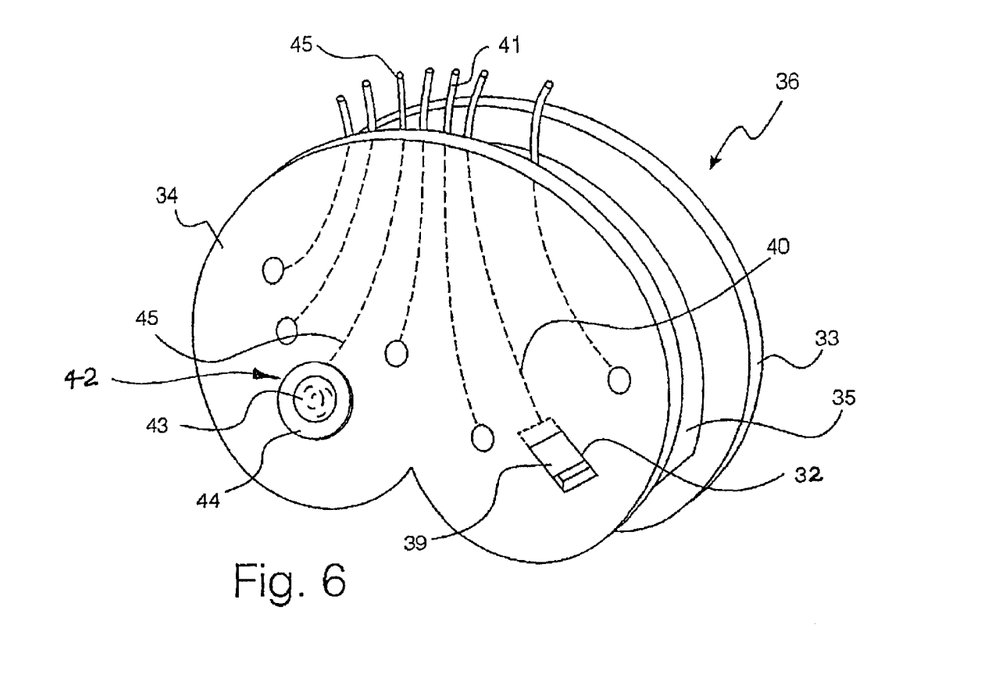
FIG. 6 is a schematic perspective view of a partition between two adjacent tanks.

FIG. 6 illustrates the form of a double-skin partition which may separate adjacent tanks in a multiple tank system such as that shown in FIG. 3. A peripheral bounding wall 35 separates two planar end walls 34, 33 to define an interior chamber. This allows one of the two end walls 34, 35 to comprise or include a semi-permeable membrane to permit the removal from the process fluid of constituents such as salt, heavy metals or other compounds. The location of the outlet 32 or transfer passage from one chamber to the next at a central point as illustrated in FIG. 6 plays its part in ensuring that the semi-permeable membrane remains clean due to the slight scouring action of the circulatory process fluid in contact with the semi-permeable membrane as it passes through the partition 36 from one chamber to the next.

This opening 32, as shown in FIG. 6, may be adjustable in size by for example the provision of an obturator plate 39 connected by a cable to a control handle 41 at the upper part of the partition, projecting above the top of the tank. By acting on the handle 41 a cable 40 is urged along its length one way or the other to vary the position of the obturator plate 39 and thus the flow cross section of the opening 32.

Between the two end plates there are also provided an array of sensors, including a microphone used as described above to detect the rate of circulating flow by the noise generated thereby. A safety pressure valve 42 is also located in the end walls, in the form of a ball 43 in a correspondingly shaped opening 44 into which it can be drawn by applying tension to a cable 45 leading out at the top of the tank adjacent the valve-opening handle 41. If a pressure differential greater than a predetermined threshold arises across the partition 36 the ball 43 is pushed out of the socket 44 to allow fluid to flow between the adjacent chambers and equalise the pressure in them or at least reduce the pressure differential. The ball 43 can be repositioned simply by applying tension to the cable 45 to cause the ball to be drawn back into the socket 44. A similar safety valve, but with a frangible outer plate, (not shown) is provided at the end walls of the row of tanks which communicate with the lagoon.

Figure 7:
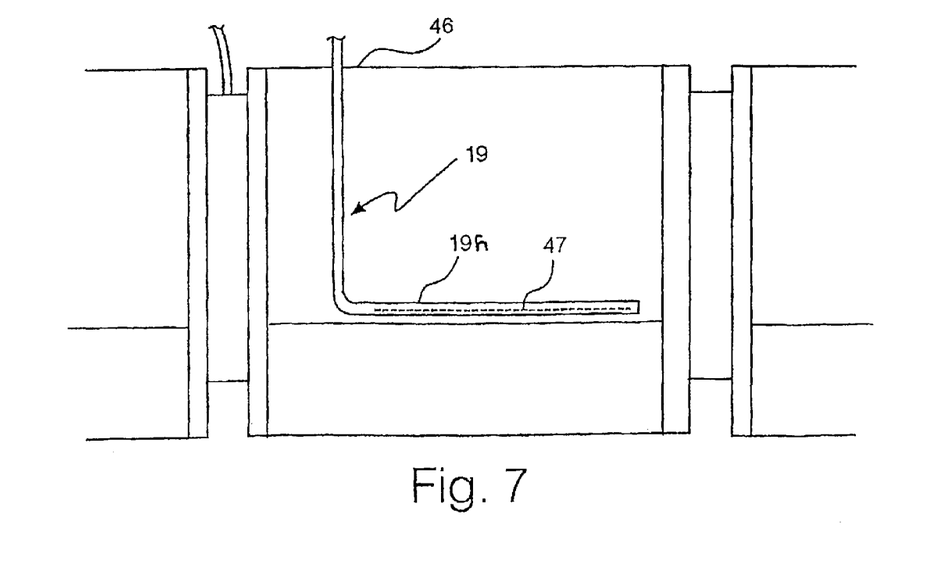
FIG. 7 is an axial sectional view of a tank structure incorporating the double-skin partition illustrated in FIG. 6.
Figure 8:
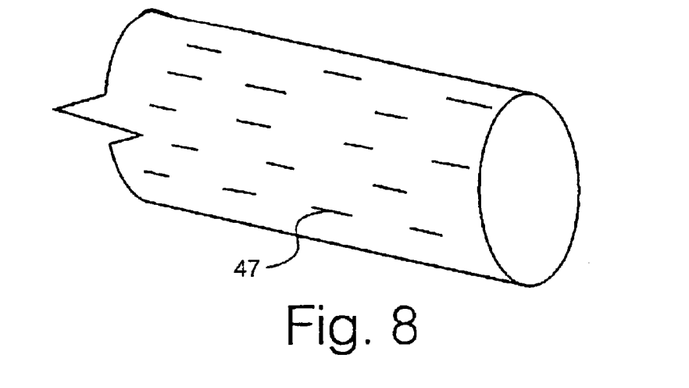
FIG. 8 is a schematic view of a gas delivery tube having slit-like exit openings.

FIGS. 7 and 8 illustrate the form of the gas delivery tube such as 19, 20 for use in an embodiment such as that illustrated where adjacent tanks are separated by double-skinned partitions as shown in FIG. 7. Here the delivery tube 19 is shown. It has a generally L-shape configuration to allow for removal through an upper opening 46 in the top of the tank. The horizontal limb 19h has a plurality; of slit-like openings 47 around its periphery. The material of the tube is slightly elastic so that the slits 47 open by the slight expansion of the tube when gas is delivered to it under a slight pressure. The openings 47 thus act as valves preventing any return flow of gas or fluid into the interior of the gas delivery tube even when no gas is delivered thereto.

Figure 9:
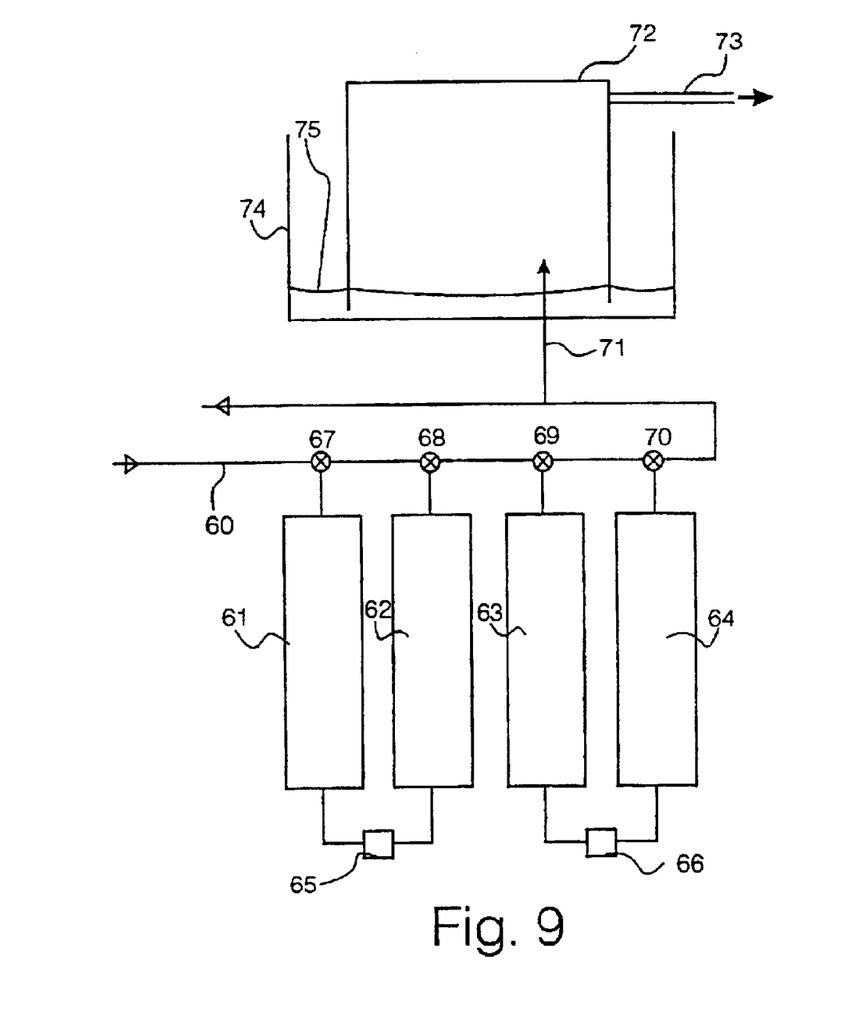
FIG. 9 is a schematic view of a gas pumping system for drawing off gas from the system.

FIG. 9 is a schematic diagram illustrating a pumping system for compressing the gas generated within the chambers, to which pipe 60 is connected. The pumping system comprises a number (in this case 4) of vertical hollow columns 61, 62, 63, 64 each partially filled with water and connected together in pairs by pumps 65, 66 at their lower ends. At their upper ends the hollow columns 61–64 are connected by valves 67, 68, 69, 70 to the pipe 60 and valve 70 is connected to a delivery pipe 71 leading to gas collection vessel 72 from which a compressed gas delivery outlet 73 leads onto a gas store (not shown).

The collection vessel 72 is in the form of an inverted 'gasometer' configuration, the rim of which enters a liquid bath 75 in an upwardly open container 74.

In operation the valves 67–70 are controlled by a control circuit (not shown) to open and close selectively whereby to allow gas to enter from the pipe 60 into one or more of the hollow columns 61–64. When the column is full the appropriate valve is closed and water is pumped by the pump 65 or 66 from the companion tube into the gas-collection tube thereby compressing the gas therein. The valves 67–70 are then opened and/or closed as appropriate to form a path for the compressed gas into the gas collection vessel 72 from where it can be drawn off via the outlet 73 as required for further processing.

What is claimed is:

1. Treatment apparatus comprising a chamber for treatment of a process fluid and having at least two regions said chamber is an elongate shape with a substantially cardioid cross section, means for causing the process fluid to follow a vortex flow-path within each of said regions, the said means for causing the process fluid to follow the vortex flow-path in each said region comprises at least one row of bubble inlets for introducing gas into the chamber along a cusp between the said two regions within the chamber to create a rising stream of bubbles acting at least in part to drive the vortex flow-path of the said process fluid within the chamber, the two regions communicating with one another such that process fluid introduced through an inlet into one region is constrained to flow into the other region before leaving the chamber, characterized in that at least part of the chamber wall in which an outlet is located is formed is formed as a semi-permeable membrane contacted intimately by the process fluid following said vortex flow-path.

2. Apparatus according to claim 1, characterized in that the inlet to the apparatus opens directly into one of the said two regions.

3. Apparatus according to claim 2, further characterized in that an outlet located in the at least part of the chamber wall communicates with the other of the said two regions, the arrangement being such that process fluid introduced into the said one region through the inlet circulates in the said one region before transferring to the other of the said two regions in which it flows in contact with the semi-permeable membrane before leaving through the outlet.

4. Apparatus according to claim 1, characterized in that the means for causing the process fluid to follow the vortex flow-path within the chamber acts between the said first and second region.

5. Apparatus according to claim 1, characterized in that at least a part of another chamber wall is formed as a semi-permeable membrane contacted by the process fluid in its vortex flow-path.

6. Apparatus according to claim 1, characterized in that all the walls defining the said chamber are semi-permeable membranes.

7. Apparatus according to claim 6, characterized in that the chamber is formed as a vessel immersed in a liquid bath or lagoon containing a liquid the composition of which encourages transfer of selected materials across the said semi-permeable membrane.

8. Apparatus according to claim 1, characterized in that there are a plurality of chambers separated from one another by double-skinned partitions themselves defining compartments housing fluids co-operating in the transfer of selected materials across the semi-permeable membrane.

9. Apparatus according to claim 1, characterized in that the said chamber is provided with heating means operable to heat a wall of the chamber in a region where the convection currents in the process fluid setup as a result of such heating travel in the same direction as the circulating vortex flow-path driven by the bubbles or other circulation-driving means.

10. Apparatus comprising a plurality of chambers according to claim 1, characterized in that a gas outlet from one chamber of the system is connected to an inlet of another chamber of the system whereby in use to transfer surplus gas from the said one chamber or generated therein, to the said other chamber.

11. Apparatus according to claim 1, characterized in that surplus gas from or generated within at least some of the chambers of the system is lead by outlet conduits to a gas compression system comprising a plurality of upright elongate chambers partially filled with a liquid the level of which is controllable by pumping means to act as a piston compressing gas trapped above it in the said upright elongate chamber.

12. Apparatus according to claim 1, characterized in that the chamber walls between adjacent chambers have pressure relief valves therein for allowing an excessive pressure differential between adjacent chambers to be relieved.

13. Apparatus according to claim 1, characterized in that the outlet from the or each chamber is positioned such that the process fluid in the chamber flows around the vortex flow-path substantially centered on the outlet such that, in use, particulate material above a certain range of dimensions and/or density is effectively filtered by the vortex acceleration of the circulating process fluid as it flows into the outlet from the chamber.

14. Apparatus according to claim 1, characterized in that the means for introducing gas into the chamber is a tube of substantially elastic material having a plurality of slit-like openings in its periphery, which open when there is a pressure differential across the tube wall with the higher pressure in the tube and close when there is a pressure differential across the tube wall with the lower pressure in the tube, whereby to act as unidirectional valves preventing a reverse flow of gas from the chamber into the tube.

* * * * *